(12) United States Patent
Pierce et al.

(10) Patent No.: US 11,097,050 B2
(45) Date of Patent: Aug. 24, 2021

(54) SENSING SYSTEM FOR MULTIPLE LUMEN TUBING

(71) Applicant: Moog Inc., Elma, NY (US)

(72) Inventors: Nate Pierce, Layton, UT (US); Larry Clayton, Farmington, UT (US); Timothy Riley, Tooele, UT (US)

(73) Assignee: Moog Inc., Elma, NY (US)

( * ) Notice: Subject to any disclaimer, the term of this patent is extended or adjusted under 35 U.S.C. 154(b) by 316 days.

(21) Appl. No.: 16/098,895

(22) PCT Filed: May 17, 2017

(86) PCT No.: PCT/US2017/033091
§ 371 (c)(1),
(2) Date: Nov. 5, 2018

(87) PCT Pub. No.: WO2017/205141
PCT Pub. Date: Nov. 30, 2017

(65) Prior Publication Data
US 2019/0192773 A1    Jun. 27, 2019

Related U.S. Application Data

(60) Provisional application No. 62/341,176, filed on May 25, 2016.

(51) Int. Cl.
*A61M 5/168* (2006.01)
*A61B 5/15* (2006.01)
(Continued)

(52) U.S. Cl.
CPC .......... *A61M 5/16886* (2013.01); *A61B 5/15* (2013.01); *A61M 5/142* (2013.01); *A61M 5/168* (2013.01);
(Continued)

(58) Field of Classification Search
CPC .. A61M 5/16886; A61M 5/168; A61M 5/142; A61M 39/08; A61M 37/00;
(Continued)

(56) References Cited

U.S. PATENT DOCUMENTS 6,454,997 B1 * 9/2002 Divino, Jr. .......... A61M 1/3621
128/DIG. 3
8,120,500 B2 * 2/2012 Tokhtuev ............ G01F 23/0007
340/618

(Continued)

FOREIGN PATENT DOCUMENTS

CN    104236649 A    12/2014
CN    105025905 A    11/2015
(Continued)

OTHER PUBLICATIONS

Stephens D.N. et al., "Multifunctional catheters combining intracardiac ultrasound imaging and electrophysiology sensing," IEEE Transactions on Ultrasonics, Ferroelectrics, and Frequency Control, vol. 55, issue 7, pp. 1570-1581, Jul. 2008.

*Primary Examiner* — Lauren P Farrar
*Assistant Examiner* — Hamza A Darb
(74) *Attorney, Agent, or Firm* — Hodgson Russ LLP

(57) ABSTRACT

A multi-lumen sensing system (10) includes medical tubing (20) having a plurality of lumens (22A, 22B) and at least one secondary passageway (24) extending in an axial direction of the medical tubing, wherein the secondary passageway is between the plurality of lumens. The multi-lumen sensing system may include a sensing receptacle (30) defining a channel (32) in which a lengthwise portion of the medical tubing is received. A plurality of ultrasonic transmitting elements (40T, 42T) may be arranged within the secondary passageway of the medical tubing or as part of the sensing receptacle for transmitting respective ultrasonic signals across the lumens to a corresponding plurality of ultrasonic (Continued)

receiving elements (40R, 42R) of the sensing receptacle. Alternatively, the sensing receptacle may include a plurality of ultrasonic transmitting and receiving elements (40, 42, 44) transmitting respective signals across the lumens for return reflection at an interface of the secondary passageway.

16 Claims, 3 Drawing Sheets

(51) Int. Cl.
| | | |
|---|---|---|
| *A61M 39/08* | (2006.01) | |
| *A61M 5/142* | (2006.01) | |
| *A61M 1/36* | (2006.01) | |
| *A61M 37/00* | (2006.01) | |

(52) U.S. Cl.
CPC .......... *A61M 39/08* (2013.01); *A61B 5/15003* (2013.01); *A61B 5/150946* (2013.01); *A61M 1/3626* (2013.01); *A61M 37/00* (2013.01); *A61M 2039/082* (2013.01); *A61M 2205/33* (2013.01)

(58) Field of Classification Search
CPC .......... A61M 2039/082; A61M 1/3626; A61M 2205/33; A61M 5/16831; A61M 5/16859; A61B 5/15; A61B 5/15003; A61B 5/150946

See application file for complete search history.

(56) References Cited

U.S. PATENT DOCUMENTS

| | | | |
|---|---|---|---|
| 2005/0209552 A1* | 9/2005 | Beck | F04B 43/1253 |
| | | | 604/67 |
| 2008/0097179 A1 | 4/2008 | Russo | |
| 2009/0049919 A1 | 2/2009 | Hills | |
| 2009/0299260 A1 | 12/2009 | Kreischer et al. | |
| 2010/0114001 A1 | 5/2010 | O'Mahony | |
| 2011/0036143 A1 | 2/2011 | Riley et al. | |
| 2012/0259208 A1 | 10/2012 | Bloom et al. | |
| 2014/0249453 A1* | 9/2014 | Wilson | A61N 7/00 |
| | | | 601/2 |
| 2014/0257090 A1 | 9/2014 | Fischer, Jr. et al. | |
| 2015/0082913 A1 | 3/2015 | Maruyama et al. | |
| 2018/0195887 A1 | 7/2018 | Wei et al. | |

FOREIGN PATENT DOCUMENTS

| | | |
|---|---|---|
| CN | 105342862 A | 2/2016 |
| EP | 2722654 A1 | 4/2014 |
| WO | 00/04943 A1 | 2/2000 |
| WO | 03047439 A2 | 6/2003 |

* cited by examiner

SENSING SYSTEM FOR MULTIPLE LUMEN TUBING

FIELD OF THE INVENTION

The invention relates to sensing fluid flow within medical tubing, specifically medical tubing having multiple lumens.

BACKGROUND OF THE INVENTION

Medical tubing is manufactured by extrusion or coextrusion of one or more biomedical grade polymers in a variety of cross-sectional shapes and with multiple lumens of various cross-sectional shapes and sizes. Multiple lumen tubing can be found in various medical devices including catheters, extension lines, transfusion devices, and monitoring devices. Multiple lumen tubing provides a plurality of conduits for efficiently transporting various fluids, including medications and contrast agents, into and out of the body. Multiple lumen tubing is also used to accommodate a guide wire and electrical wiring for mechanically positioning and providing power to diagnostic and therapeutic devices in the body.

In some medical applications, it is important to detect the presence and size of constituents carried by the fluid, for example air bubbles within a liquid. It is known to monitor flow through single lumen tubing using a pair of piezoelectric ultrasonic elements. A first piezoelectric element arranged on one side of the tubing is energized and transmits an acoustic signal at an ultrasonic frequency across the tubing transversely through the lumen carrying the fluid. A second piezoelectric element arranged on an opposite side of the tubing receives the acoustic signal after the acoustic waves have interacted with matter between the piezoelectric elements, and generates a voltage signal corresponding to the received acoustic signal. An illustration of this known single lumen sensing arrangement is shown in FIG. 1. The voltage signal generated by the receiving piezoelectric element may be analyzed to indicate the presence and size of constituents (e.g. air bubbles) carried by the fluid. The large difference in acoustic impedance between liquid flowing in the lumen and an air bubble in the liquid results in reflection and scattering of the acoustic waves, thereby weakening the signal generated by the receiving element. This phenomenon may be used to detect the presence and size of air bubbles in the liquid. This single lumen tubing method is not effective for multiple lumen tubing because each lumen cannot be sensed individually.

In some medical applications, fluid flow through the medical tubing is monitored to measure flow parameters such as flow velocity. A known arrangement for measuring flow velocity in single lumen tubing is shown in FIG. 2. The transmitting and receiving piezoelectric elements are oriented on an acoustic communication axis at an acute angle relative to the fluid flowing in the tubing. The speed at which the fluid is flowing is superimposed upon the sound propagation speed of the acoustic signal. To cancel out the sound propagation speed, the acoustic signal is transmitted in the direction of the flow and then the receiving and transmitting elements are reversed so the acoustic signal is transmitted in the direction opposite to the flow direction. The flow velocity is proportional to the inverse of the difference between propagation time in the flow direction and the propagation time opposite the flow direction. Here again, the single lumen tubing method is not effective for multiple lumen tubing because each lumen cannot be sensed individually.

SUMMARY OF THE INVENTION

A multi-lumen sensing system is provided for fluid sensing in a plurality of lumens of multi-lumen medical tubing. The medical tubing includes at least one secondary passageway in addition to the plurality of fluid-carrying lumens, wherein the secondary passageway is between the plurality of lumens. The multi-lumen sensing system may further comprise a sensing receptacle defining a channel or other type of passage in which a lengthwise portion of the medical tubing is received.

In one embodiment, the at least one secondary passageway contains a plurality of transmitting elements each transmitting a respective ultrasonic signal across a corresponding one of the plurality of lumens, and the sensing receptacle includes a plurality of receiving elements respectively corresponding to the plurality of transmitting elements. Each of the plurality of receiving elements is arranged to receive the respective ultrasonic signal from a corresponding one of the plurality of transmitting elements after the ultrasonic signal has passed through a corresponding lumen. The plurality of transmitting elements may be arranged within a single secondary passageway, and an acoustic damping member may be arranged between the plurality of transmitting elements to maximize attenuation and stifle propagation of acoustic waves in a direction toward an unassociated lumen.

In another embodiment, the sensing receptacle includes a plurality of transmitting elements each transmitting a respective ultrasonic signal across a corresponding lumen, and a plurality of receiving elements respectively corresponding to the transmitting elements. Each of receiving elements is arranged to receive the respective ultrasonic signal from a corresponding one of the transmitting elements after the ultrasonic signal has passed through the particular lumen. The respective ultrasonic signals transmitted by the transmitting elements may be directed to propagate parallel to one another through different lumens.

In a further embodiment, the sensing receptacle includes a plurality of transmitting and receiving elements each transmitting a respective ultrasonic signal across a corresponding lumen and also receiving the ultrasonic signal after the signal reflects in a return direction at an interface of the at least one secondary passageway and passes again through the lumen. The at least one secondary passageway may contain an acoustic isolation medium, for example air, to acoustically isolate the plurality of lumens from one another.

The multi-lumen sensing system may further comprise an electronic control unit connected to the transmitting elements and the receiving elements, wherein the control unit is configured to drive the plurality of transmitting elements and to receive output voltage signals from the plurality of receiving elements. The electronic control unit may be configured to drive each of the transmitting elements at a unique respective frequency different from the drive frequencies of other transmitting elements.

BRIEF DESCRIPTION OF THE DRAWING VIEWS

For a fuller understanding of the nature and objects of the invention, reference is made to the following detailed description taken in conjunction with the accompanying drawings, in which.

Figure 3:
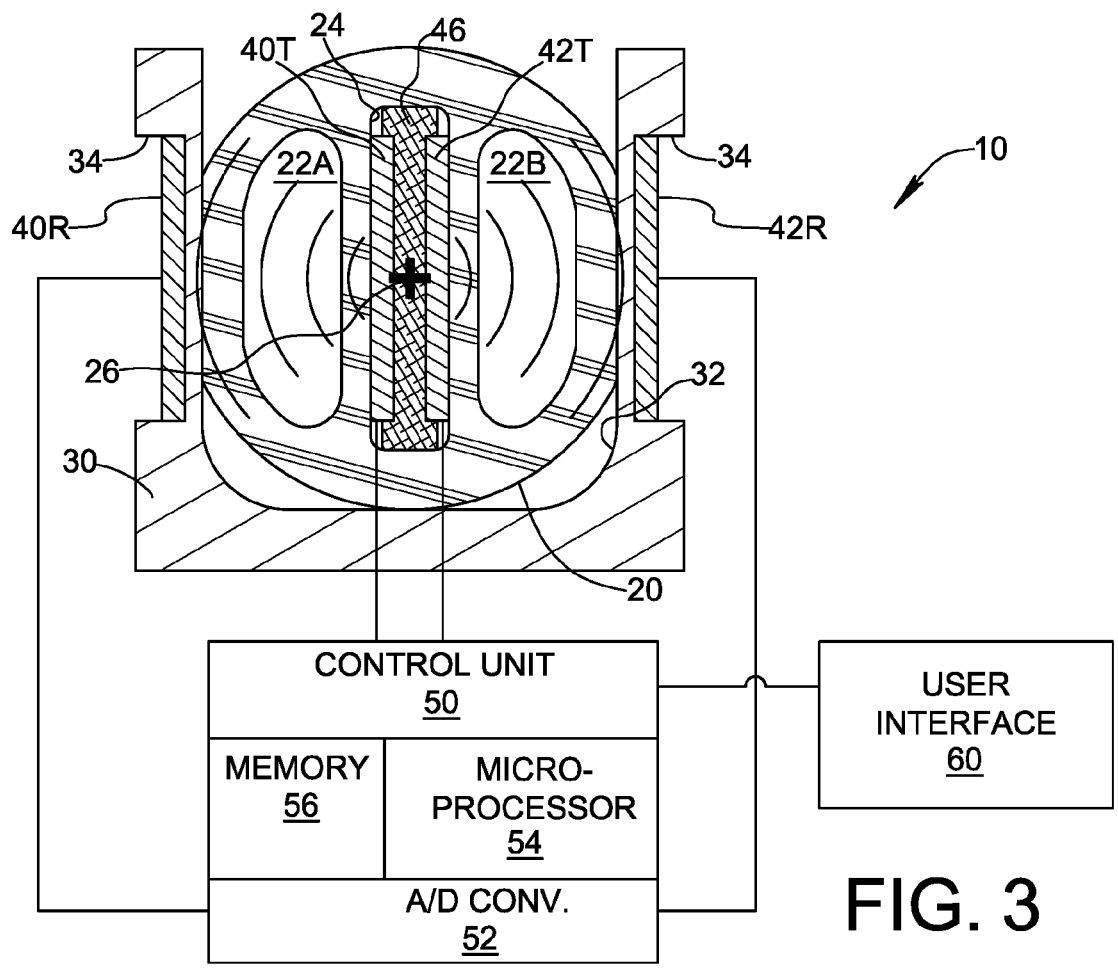
Figure 4:
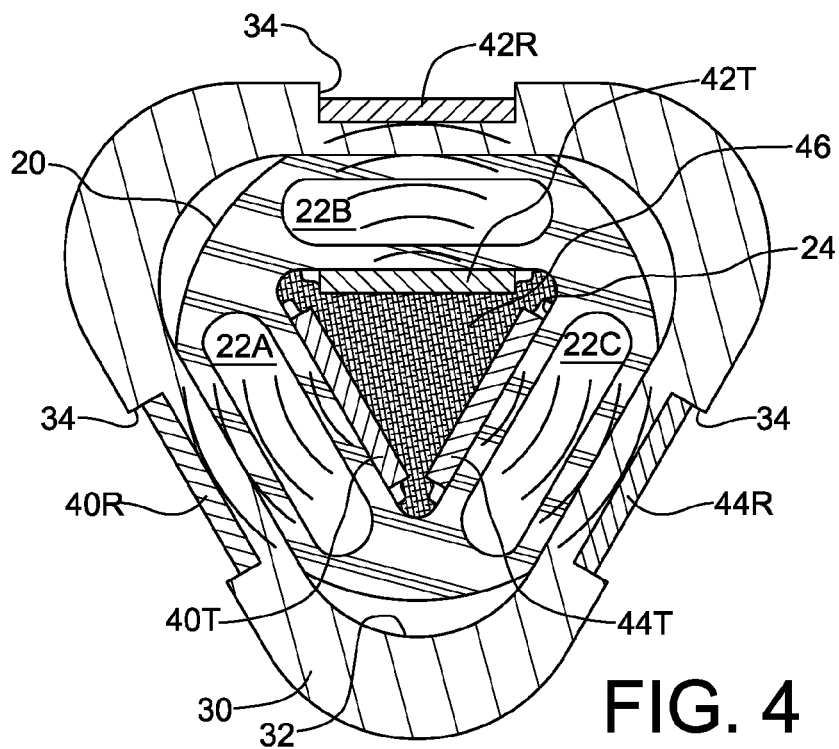
Figure 5:
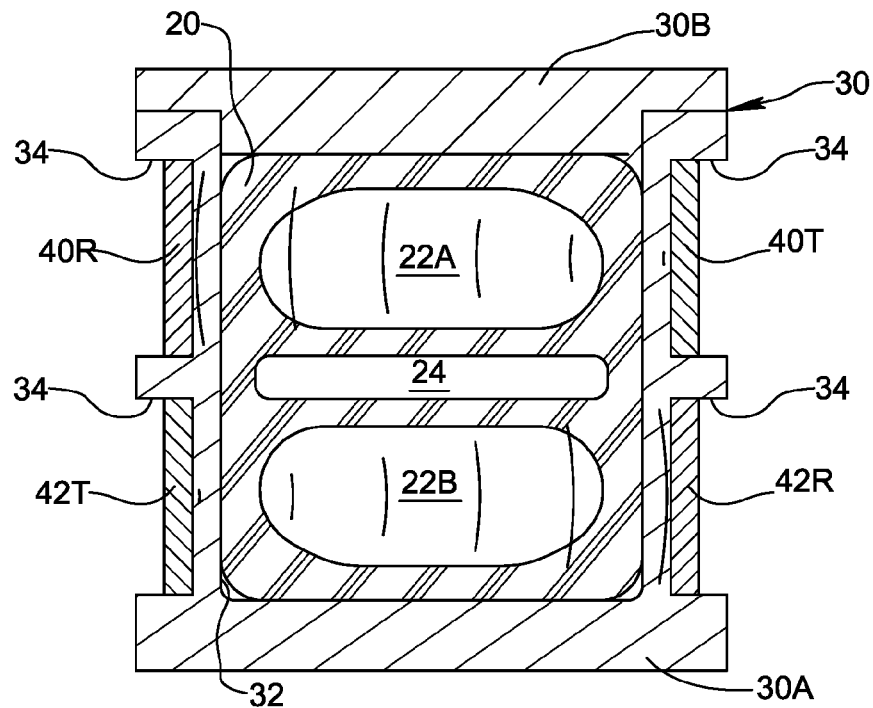
Figure 6:
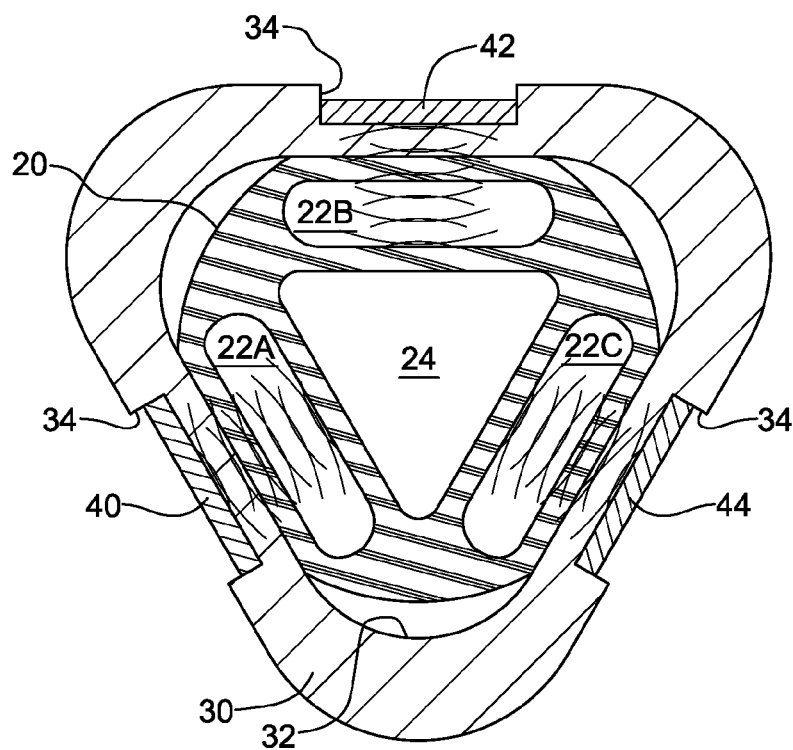

FIG. 3 schematically shows a multiple lumen fluid sensing system according to an embodiment of the present invention, wherein multiple lumen tubing and a tubing receptacle of the system are shown in cross-section;

FIG. 4 is a cross-sectional view of multiple lumen tubing and a tubing receptacle illustrating another embodiment of the present invention;

FIG. 5 is a cross-sectional view of multiple lumen tubing and a tubing receptacle illustrating a further embodiment of the present invention; and FIG. 6 is a cross-sectional view of multiple lumen tubing and a tubing receptacle illustrating yet another embodiment of the present invention.

DETAILED DESCRIPTION OF THE INVENTION

FIG. 3 depicts a system 10 for sensing fluid flow within respective lumens of multiple lumen tubing 20 according to an embodiment of the present invention. The multiple lumen tubing 20, shown in cross-section in FIG. 3, comprises a plurality of sensed lumens 22A, 22B which may be used as conduits for flowing fluids. The plurality of sensed lumens 22A, 22B may have different respective cross-sectional shapes and sizes, or may have identical dimensions. The multiple lumen tubing 20 may further comprise a secondary passageway 24 for purposes described below. As may be understood, multiple lumen tubing 20 extends longitudinally into and out of the plane of drawing FIG. 3 along a central longitudinal axis 26, and may be flexible to define a non-linear flow path.

System 10 further comprises a sensing receptacle 30 defining a channel or other type of passage 32 sized to receive a lengthwise portion of multiple lumen tubing 20. In FIG. 3, sensing receptacle 30 has an open U-shaped configuration allowing the portion of tubing 20 to be inserted into the receptacle in a direction perpendicular to longitudinal axis 26 of tubing 20. As will be apparent later from description of alternative embodiments, receptacle 30 may have a closed configuration completely surrounding the received portion of tubing 20, wherein the tubing is threaded through the passage 32 of receptacle 30 in a direction coinciding with longitudinal axis 26 of tubing 20. A hybrid sensing receptacle 30 may be provided that is closed during use but has a movable segment (e.g. a hinged or sliding door, or a temporarily removable segment) operable to open the receptacle to facilitate loading of a portion of multiple lumen tubing 20 into the receptacle. Channel or passage 32 may be dimensioned for slight interference fit with the received portion of tubing 20 to give the flexible multiple lumen tubing a press fit for good acoustic propagation. Sensing receptacle 30 may be integral with a medical device, such as a transfusion device. Alternatively, sensing receptacle 30 may be physically separate from a medical device but equipped to communicate wirelessly or by wired connection with the medical device. As another alternative, sensing receptacle 30 may be a standalone device equipped with a display or other means to output sensing results to a user.

System 10 further comprises a plurality of ultrasonic sensing elements 40T, 40R, 42T, 42R. The plurality of ultrasonic sensing elements may be piezoelectric ultrasonic elements. Rectangular or square thickness mode piezoelectric plate elements are suitable for practicing the invention, and are commercially available in width and length dimensions ranging from 1 mm to 120 mm, with thicknesses down to 0.2 mm. The resonant frequency for the ultrasonic sensing elements may be up to about 10 MHz. The sensing elements may be made using any suitable piezoelectric material, including but not limited to piezoelectric single crystal materials, polymeric piezoelectric materials, and other polycrystalline piezoelectric materials of various compositions. By way of non-limiting example, soft lead zirconate titanate (PZT-5A) sensing elements available from Morgan Advanced Materials having a resonant frequency of about 2 MHz may be used. Examples of similar sensing elements include EC-65 from EDO, a subsidiary of Harris Corp., C5500 from Channel, and PICC 255 from PI Ceramic. Of course, other piezoelectric sensing elements are available from a variety of sources and may be used in practicing the present invention. Elements operating at a higher frequency generate higher resolution for bubble detection, but the acoustic signal also attenuates more quickly, thereby limiting transmission range. The transmitter and receiver piezoelectric materials may be different. "Hard" PZT ceramics generally work best for transmitters while the "soft" PZT ceramics are generally best for receivers.

In the embodiment shown in FIG. 3, the sensing elements are arranged in pairs such that one sensing element of the pair transmits an acoustic signal and the other sensing element of the pair receives the acoustic signal. Each pair of sensing elements is assigned to a respective lumen. More specifically, sensing elements 40T, 40R are assigned to sensed lumen 22A, whereas sensing elements 42T, 42R are assigned to sensed lumen 22B.

As shown in FIG. 3, sensing elements 40T, 42T may be operated as transmitting elements and may be arranged internally within secondary passageway 24 such that their respective acoustic signals are directed radially outward from central axis 26. An acoustic damping member 46 may be positioned within secondary passageway 24 between sensing elements 40T, 42T. The material(s) of damping member 46 may be selected to provide an acoustically lossy region between sensing elements 40T, 42T to maximize attenuation and stifle propagation of acoustic waves generated by sensing elements 40T, 42T in a direction toward the unassociated lumen, thereby isolating the sensing elements associated with one lumen from the sensing elements associated with another lumen. The transmitting elements 40T, 42T may vibrate at different frequencies or the same frequency. The use of different frequencies provides a basis to differentiate between the multiple lumens. For example, the operating frequency of a particular transmitting element 40T or 42T may be selected based on properties of the fluid expected to flow within the corresponding lumen 22A or 22B and/or the type of sensing being conducted. The acoustic signal transmitted by sensing element 40T is received by paired sensing element 40R after having passed transversely through lumen 22A. Likewise, the acoustic signal transmitted by sensing element 42T is received by paired sensing element 42R after having passed transversely through lumen 22B.

In the embodiment shown in FIG. 3, receiving elements 40R, 42R are arranged within receptacle 30 to respectively face paired sensing elements 40T, 42T. For example, receiving elements 40R, 40T may be mounted in corresponding recesses 34 in receptacle 30. The exterior of multiple lumen tubing 20 may include one or more markings or indicia to enable a user to properly locate and align the sensed tubing portion as it is loaded into receptacle 30 so that communication between paired sensing elements is ensured. Alternatively, or additionally, the external shape of the sensed portion of tubing 20 may be configured to fit within channel or passage 32 of receptacle 30 in only one possible orientation, thereby ensuring proper alignment and communication between paired sensing elements. In addition to the mechanical techniques mentioned above, alignment may also be achieved electro-acoustically. The response of the receiver element will peak when the transmitting element is optimally located and aligned opposite it. This allows the user to monitor the receiver element signal to determine when the transmitting and receiving elements are properly aligned. This approach to alignment may be automated or an auditory signal could be used to indicate when optimal alignment has been achieved.

System 10 may also comprise an electronic control unit 50 connected to the various sensing elements of system 10. Control unit 50 drives the transmitting elements of system 10 and receives output voltage signals from the receiving elements As shown in FIG. 3, transmitting elements 40T, 42T and receiving elements 40R, 42R may each be connected to control unit 50. Control unit 50 may send drive signals to sensing elements 40T, 42T, and may receive output signals from sensing elements 40R, 42R. Control unit 50 may include an analog-to-digital converter 52 for digitizing the analog voltage signals from sensing elements 40R, 42R, one or more microprocessors 54 for performing calculations based on the digitized signal information, and one or more memory modules 56 for storing programming instructions, calibration parameters, and sensing measurement data associated with the respective lumens of tubing 20. Control unit 50 may be connected to a user interface 60, which may be part of an associated medical device or a dedicated standalone user interface.

The particular sensing routines and algorithms executed by control unit 50 are subject to wide variation. As mentioned above, routines and algorithms are already known to persons skilled in the art for detecting the presence and size of constituents within fluid flowing through single lumen tubing, and for measuring flow velocity of the fluid. Such routines and algorithms may be adapted and utilized for the respective sensed lumens monitored by system 10.

Figure 1:
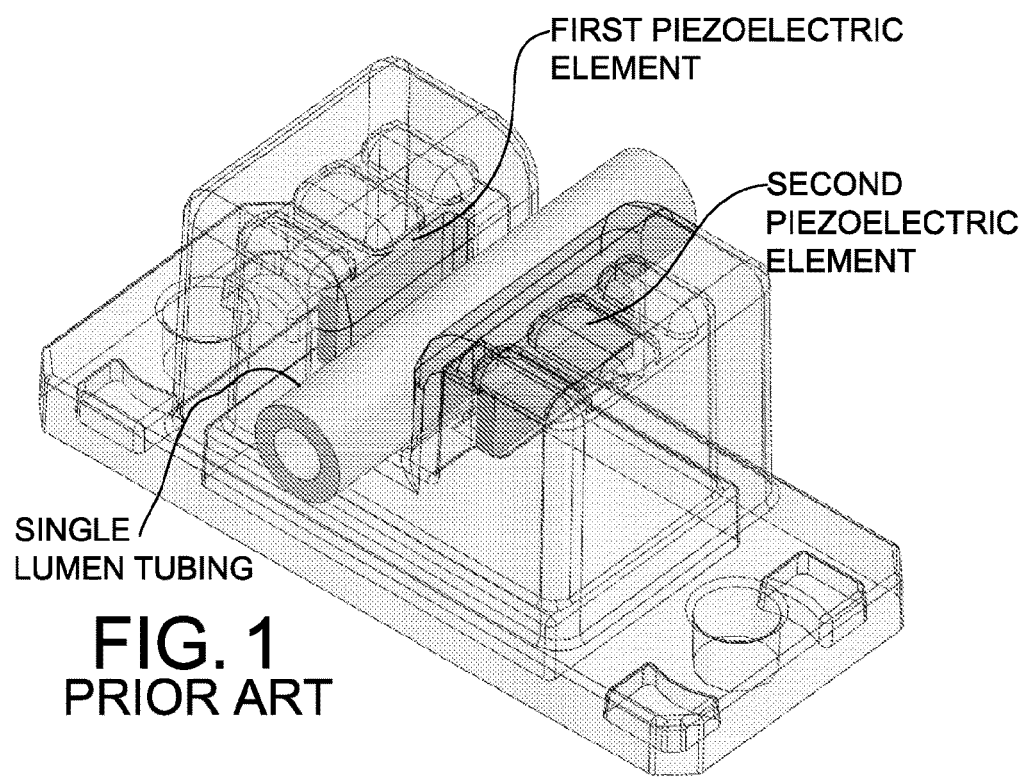
FIG. 1 depicts a single lumen fluid sensing system according to the prior art for detecting constituents in fluid flowing through the lumen.
Figure 2:
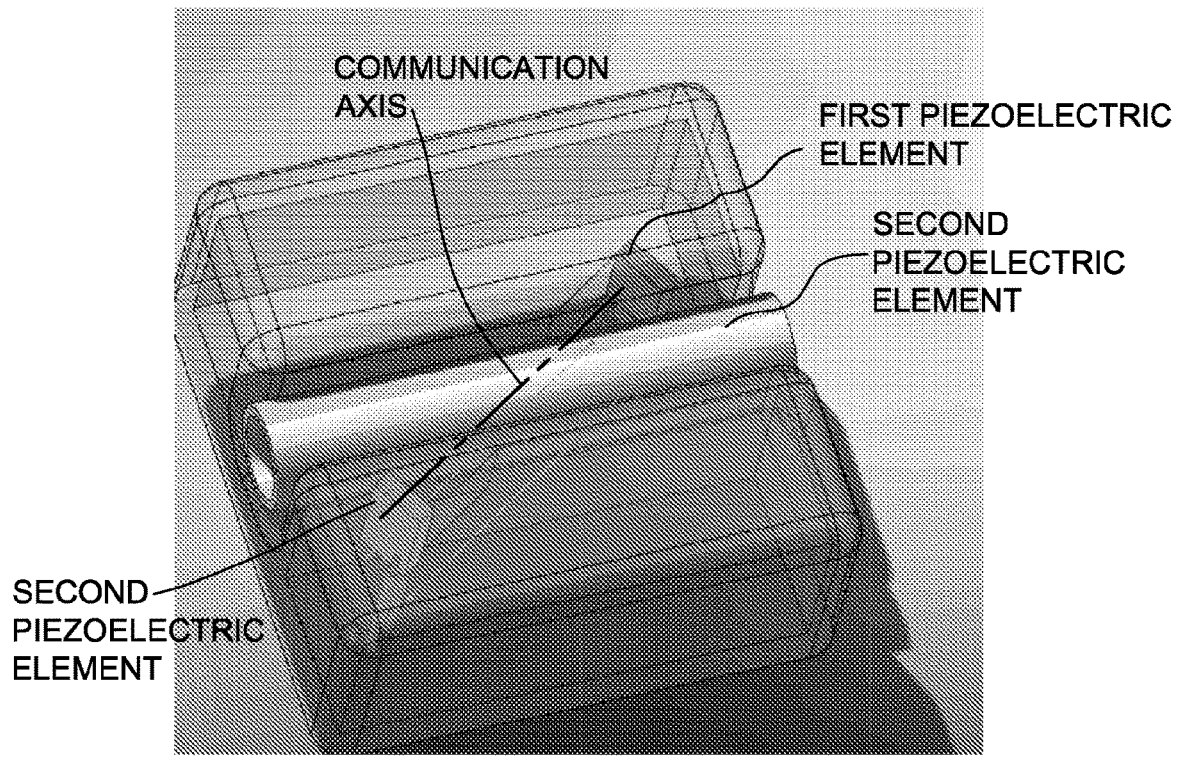
FIG. 2 depicts a single lumen fluid sensing system according to the prior art for measuring flow velocity of fluid flowing through the lumen.

The directional arrangement of sensing elements 40T, 40R with respect to sensed lumen 22A, and the directional arrangement of sensing elements 42T, 42R with respect to sensed lumen 22B, are illustrated in FIG. 3 as being perpendicular to the longitudinal axis 26 of tubing 20 for detecting fluid constituents such as air bubbles. Similar directional arrangements of sensing elements are illustrated in FIGS. 4 through 6 showing further embodiments described below. It will be understood that in all embodiments of this specification, the directional arrangement of sensing elements may be altered for any or all lumens in multiple lumen tubing 20 as suggested by FIG. 2 so that the sensing elements face each other along a communication axis oriented at an acute angle relative to the tubing axis 26 for measurement of flow velocity.

Further embodiments of the invention will now be described with reference to FIGS. 4 through 6. Control unit 50 and user interface 60 are omitted from the drawing figures and description to avoid repetition.

Turning now to FIG. 4, an alternative embodiment of system 10 is shown wherein multiple lumen tubing 20 has three sensed lumens 22A, 22B, 22C angularly spaced about tubing axis 26. Secondary passageway 24 may have a substantially triangular cross-sectional shape, and a plurality of transmitting elements 40T, 42T, 44T may be arranged against corresponding flat surfaces of secondary passageway 24 such that each transmitting element faces radially outward toward a respective lumen 22A, 22B, 22C. As in the previous embodiment, an acoustic damping member 46 may be positioned within secondary passageway 24 to provide acoustic isolation among the sensing elements. The multiple lumen tubing 20 is received by passage 32 of receptacle 30. Passage 32 may define a triangular inner wall, and a plurality of receiving elements may 40R, 42R, 44R may be located in recesses 34 of receptacle 30 to face their associated transmitting elements 40T, 42T, 44T across respective lumens 22A, 22B, 22C.

Reference is now made to FIG. 5. The embodiment shown in FIG. 5 differs from the previous embodiments of FIGS. 3 and 4 because the embodiment of FIG. 5 avoids internally mounted sensing elements within secondary passageway 24. Receptacle 30 may have a U-shaped base 30A mated with a removable cover 30B. Passage 32 of receptacle 30 receives multiple lumen tubing 20, which is configured generally as shown in FIG. 3 with two lumens 22A, 22B and secondary passageway 24 in between the lumens. However, secondary passageway 24 does not contain any sensing elements, and may be filled with air or another medium to acoustically isolate the two lumens 22A, 22B. Receptacle 30 may include recesses 34 for mounting a first pair of sensing elements 40T, 40R across lumen 22A, and a second pair of sensing elements across lumen 22B. The communication axis between sensing elements 40T, 40R is essentially parallel to the communication axis between sensing elements 42T, 42R, however the direction of propagation is reversed between the two sensing element pairs. One skilled in the art will realize that further parallel sensing element pairs may be added to sense additional lumens.

In the embodiments shown in FIGS. 3 through 5, the location of the transmitting and receiving sensing elements may be swapped for any or all the lumens, i.e. the location of each receiving element 40R, 42R, 44R may be swapped with the location of the corresponding transmitting element 40T, 42T, 44T. Thus, any or all of the receiving elements 40R, 42R, 44R may be located within secondary passageway 24, and the corresponding transmitting element(s) 40T, 42T, 44T may be located in receptacle 30.

FIG. 6 shows another embodiment of the present invention that operates in pulse-echo mode similar to SONAR, whereby a single sensing element acts as both a transmitting element and a receiving element. For sake of illustration, FIG. 6 shows a triangular receptacle 30 and three lumen tubing 20 similar to those shown in FIG. 4, however other receptacle and tubing configurations are of course possible. Secondary passageway 24 may be filled with air or another medium having an acoustic impedance substantially different from the acoustic impedance of the material of tubing 20 and the fluid flowing through lumens 22A, 22B, 22C to promote acoustic reflection.

As will be appreciated from FIG. 6, only single-sided access to each lumen 22A, 22B, 22C is needed when the pulse-echo technique is used. An acoustic pulse generated by each sensing element 40, 42, 44 is transmitted through the corresponding lumen 22A, 22B, 22C, and, upon reaching the interface of secondary passageway 24, is reflected back toward the sensing element 40, 42, 44 from which the pulse originated.

An advantage of a pulse-echo configuration is that a single sensing element is required for each lumen in which fluid flows, as opposed to transmitting and receiving element pairs used in prior configurations. Moreover, all sensing elements may be mounted externally from tubing 20 in receptacle 30.

As will be appreciated, the present invention may be adapted and extended to provide lumen-specific sensing in multiple lumen tubing having more than three fluid flow lumens. For instance, whereas the triangular embodiments shown in FIGS. 4 and 6 illustrate sensing for three lumens, other polygonal shapes may serve as the basis for sensing a greater number of lumens (e.g. a hexagonal shape may be used to sense six lumens).

With respect to all embodiments, different frequencies may be assigned to each lumen such that each lumen is sensed using a frequency unique to that particular lumen.

While the invention has been described in connection with exemplary embodiments, the detailed description is not intended to limit the scope of the invention to the particular forms set forth. The invention is intended to cover such alternatives, modifications and equivalents of the described embodiment as may be included within the scope of the invention.

What is claimed is:

1. A multi-lumen sensing system (10) comprising medical tubing (20) including a plurality of lumens (22A, 22B) and at least one secondary passageway (24) extending in an axial direction of the medical tubing (20), wherein each secondary passageway (24) is between the plurality of lumens (22A, 22B);
   wherein the plurality of lumens extend parallel to one another and parallel to the secondary passageway;
   wherein the multi-lumen sensing system (10) further comprises a sensing receptacle (30) defining a passage (32) in which a lengthwise portion of the medical tubing (20) is received; and
   wherein the at least one secondary passageway (24) contains a plurality of transmitting elements (40T, 42T) each transmitting a respective ultrasonic signal across a corresponding one of the plurality of lumens (22A, 22B), and the sensing receptacle (30) includes a plurality of receiving elements (40R, 42R) respectively corresponding to the plurality of transmitting elements (40T, 42T), each of the plurality of receiving elements (40R, 42R) being arranged to receive the respective ultrasonic signal from a corresponding one of the plurality of transmitting elements (40T, 42T) after the ultrasonic signal has passed through the corresponding one of the plurality of lumens (22A, 22B).

2. The multi-lumen sensing system (10) according to claim 1, wherein the at least one secondary passageway (24) contains an acoustic isolation medium to acoustically isolate the plurality of lumens (22A, 22B) from one another.

3. The multi-lumen sensing system (10) according to claim 2, wherein the acoustic isolation medium has an acoustic impedance different from an acoustic impedance of a material from which the medical tubing (20) is formed.

4. The multi-lumen sensing system (10) according to claim 3, wherein the acoustic isolation medium is air.

5. The multi-lumen sensing system (10) according to claim 1, wherein the at least one secondary passageway (24) is a single secondary passageway containing the plurality of transmitting elements (40T, 42T).

6. The multi-lumen sensing system (10) according to claim 5, further comprising an acoustic damping member (46) within the secondary passageway (24) between the plurality of transmitting elements (40T, 42T).

7. The multi-lumen sensing system (10) according to claim 1, further comprising an electronic control unit (50) connected to the plurality of transmitting elements (40T, 42T) and the plurality of receiving elements (40R, 42R), wherein the control unit (50) is configured to drive the plurality of transmitting elements (40T, 42T) and to receive output voltage signals from the plurality of receiving elements (40R, 42R).

8. The multi-lumen sensing system (10) according to claim 7, wherein the electronic control unit (50) is configured to drive the plurality of transmitting elements (40T, 42T) at a plurality of respective frequencies, each of the plurality of respective frequencies being unique.

9. The multi-lumen sensing system (10) according to claim 1, wherein the lengthwise portion of the medical tubing (20) received by the passage (32) has an external shape configured to fit within the passage (32) in only one possible orientation.

10. A multi-lumen sensing system (10) comprising medical tubing (20) including a plurality of lumens (22A, 22B) and at least one secondary passageway (24) extending in an axial direction of the medical tubing (20), wherein each secondary passageway (24) is between the plurality of lumens (22A, 22B);
   wherein the plurality of lumens extend parallel to one another and parallel to the secondary passageway;
   wherein the multi-lumen sensing system (10) further comprises a sensing receptacle (30) defining a passage (32) in which a lengthwise portion of the medical tubing (20) is received; and
   wherein the sensing receptacle (30) includes a plurality of transmitting elements (40T, 42T) each transmitting a respective ultrasonic signal across a corresponding one of the plurality of lumens (22A, 22B), and a plurality of receiving elements (40R, 42R) respectively corresponding to the plurality of transmitting elements (40T, 42T), each of the plurality of receiving elements (40R, 42R) being arranged to receive the respective ultrasonic signal from a corresponding one of the plurality of transmitting elements (40T, 42T) after the ultrasonic signal has passed through the corresponding one of the plurality of lumens (22A, 22B).

11. The multi-lumen sensing system (10) according to claim 10, wherein the respective ultrasonic signals transmitted by the plurality of transmitting elements (40T, 42T) are directed to propagate parallel to one another.

12. The multi-lumen sensing system (10) according to claim 10, further comprising an electronic control unit (50) connected to the plurality of transmitting elements (40T, 42T) and the plurality of receiving elements (40R, 42R), wherein the control unit (50) is configured to drive the plurality of transmitting elements (40T, 42T) and to receive output voltage signals from the plurality of receiving elements (40R, 42R).

13. The multi-lumen sensing system (10) according to claim 12, wherein the electronic control unit (50) is configured to drive the plurality of transmitting elements (40T, 42T) at a plurality of respective frequencies, each of the plurality of respective frequencies being unique.

14. A multi-lumen sensing system (10) comprising medical tubing (20) including a plurality of lumens (22A, 22B) and at least one secondary passageway (24) extending in an axial direction of the medical tubing (20), wherein each secondary passageway (24) is between the plurality of lumens (22A, 22B);
   wherein the plurality of lumens extend parallel to one another and parallel to the secondary passageway;
   wherein the multi-lumen sensing system (10) further comprises a sensing receptacle (30) defining a passage

(32) in which a lengthwise portion of the medical tubing (20) is received; and wherein the sensing receptacle (30) includes a plurality of transmitting and receiving elements (40, 42, 44) each transmitting a respective ultrasonic signal across a corresponding one of the plurality of lumens (22A, 22B) and receiving the respective ultrasonic signal after reflection of the respective ultrasonic signal at an interface of the at least one secondary passageway (24) and passage of the reflected ultrasonic signal through the corresponding one of the plurality of lumens (22A, 22B).

15. The multi-lumen sensing system (10) according to claim 14, further comprising an electronic control unit (50) connected to the plurality of transmitting and receiving elements (40, 42, 44) wherein the control unit (50) is configured to drive the plurality of transmitting and receiving elements (40, 42, 44) and to receive output voltage signals from the plurality of transmitting and receiving elements (40, 42, 44).

16. The multi-lumen sensing system (10) according to claim 15, wherein the electronic control unit (50) is configured to drive the plurality of transmitting and receiving elements (40, 42, 44) at a plurality of respective frequencies, each of the plurality of respective frequencies being unique.

* * * * *